US007294477B2

(12) United States Patent
Pfeffer et al.

(10) Patent No.: US 7,294,477 B2
(45) Date of Patent: Nov. 13, 2007

(54) ALLERGEN AND TREATMENT

(75) Inventors: Alexander Terrance Pfeffer, Upper Hutt (NZ); Charles Bix Shoemaker, Upper Hutt (NZ)

(73) Assignee: Ovita Limited, Dunedin (NZ)

( * ) Notice: Subject to any disclaimer, the term of this patent is extended or adjusted under 35 U.S.C. 154(b) by 581 days.

(21) Appl. No.: 10/258,185

(22) PCT Filed: Apr. 19, 2001

(86) PCT No.: PCT/NZ01/00065

§ 371 (c)(1),
(2), (4) Date: Apr. 8, 2003

(87) PCT Pub. No.: WO01/79281

PCT Pub. Date: Oct. 25, 2001

(65) Prior Publication Data

US 2004/0214172 A1    Oct. 28, 2004

(30) Foreign Application Priority Data

Apr. 19, 2000   (NZ) .................................... 504096

(51) Int. Cl.
*G01N 33/569*  (2006.01)
*G01N 33/543*  (2006.01)
*G01N 33/53*  (2006.01)

(52) U.S. Cl. ..................... 435/7.22; 436/503; 436/504; 436/518; 436/536; 436/542; 436/501; 435/7.92

(58) Field of Classification Search ................ 436/501, 436/503, 518; 435/7.22
See application file for complete search history.

(56) References Cited

U.S. PATENT DOCUMENTS 5,795,862 A    8/1998    Frank et al.

OTHER PUBLICATIONS

Bany, J., et al. (1995) Comparison of Local and Systemic Responsiveness of Lymphocytes in vitro to *Bovicola ovis* Antigen and Concanavalin A in B. ovis-Infested and Naïve Lambs. Int. J. Parasitol. 25(12):1499-1504.
Bany, J., et al. (1995) Proliferative Responses of Lymphocytes in *Bovicola ovis*-infested Lambs. Int. J. Parasitol. 25(6):765-768.
Cleland, P. C., et al. (1989) Rate of spread of sheep lice (*Damalinia ovis*) and their effects on wool quality. Aus. Vet. J. 66(9):298-299.
Heath, A. C. G., et al. (1995) Evidence for the role of the sheep biting-louse *Bovicola ovis* in producing cockle, a sheep pelt defect. Vet. Parasit. 59:53-58.
Heath, A. C. G., et al. (1995) Preliminary investigations into the aetiology and treatment of cockle, a sheep pelt defect. Vet. Parasit. 56:239-254.
Johnson, P. W., et al. (1993) Prevalence of the causes of fleece derangement among sheep flocks in New South Wales. Aus. Vet. J. 70(6):220-224.
Kettle, P. R. and Lukies J. M. (1984) Recovery of sheep lice (*Damalinia ovis*) from baled wool: a technique enabling nationwide surveillance of louse ridden flocks. New Zealand J. Exp. Agric. 12:39-42.
Kettle, P. R. and Lukies, J. M. (1982) Effects of sheep lice (*Damalinia ovis*) on wool colour. New Zealand J. Exp. Agric. 10:15-17.
Lipson, M. and Bacon-Hall, R. E. (1976) Some Effects of Various Parasite Populations in Sheep on the Processing Performance of Wool. Wool Tech. Sheep Breeding p. 18-20.
McLeod, R. S. (1995) Costs of Major Parasites to the Australian Livestock Industries. Int. J. Parasitol. 25(11):1363-1367.
Pfeffer, A., et al. (1994) Hypersensitivity skin testing of lambs infested with the biting louse (*Bovicola ovis*). New Zealand Vet. J. 42:76.
Pfeffer, A., et al. (1997) Detection of homocytotropic antibody in lambs infested with the louse, *Bovicola ovis*, using a basophil histamine-release assay. Vet. Immunol. Immunopath. 57:315-325.
Seymour-Jones (1913) Chapter VII "Cockle" in Sheepskins. In Leather Trader Review. London p. 204-221.
Bany, J. et al. (1995) "Comparison of local and systemic responsiveness of lymphocytes in vitro to *Bovicola ovis* antigen and concanavalin A in *B. ovis*-infested and naïve lambs" *International Journal for Parasitology* 25:1499-1504.
Bany, J. et al. (1995) "Proliferative responses of lymphocytes in *Bovicola ovis*-infested lambs" *International Journal for Parasitology* 25:765-768.
Heath, A.C.G. et al. (1995) "Evidence for the role of the sheep biting-louse *bovicola ovis* in producing cockle, a sheep pelt defect" *Veterinary Parasitology* 59:53-58.
Levot, G.W. (1995) "Resistance and the control of sheep ectoparasites" *International Journal for Parasitology* 25:1355-1362.
Mumcuoglu, K.Y. et al. (1996) "Immunogenic proteins in the body and faecal material of the human body louse, *Pediculus humanus*, and their homology to antigens of other lice species" *Medical and Veterinary Entomology* 10:105-107.
Pfeffer, A. et al. (1997) "Detection of homocytotropic antibody in lambs infested with the louse, *Bovicola ovis*, using a basophil histamine-release assay" *Veterinary Immunology and Immunopathology* 57:315-325.
Shaw, R.J. et al. (1996) "Production and characterization of monoclonal antibodies recognizing ovine IgE" *Veterinary Immunology and Immunopathology* 51:235-251.

(Continued)

*Primary Examiner*—Christina Chan
*Assistant Examiner*—F. Pierre VanderVegt
(74) *Attorney, Agent, or Firm*—Knobbe, Martens, Olson & Bear LLP

(57)    ABSTRACT

The present invention is related to novel nucleoli sequences encoding a louse allergen and a methods for diagnosing, treating and preventing lice infestation and associated allergic disease with the nucleoli sequences and protein allergen of the invention. The present invention also relates to kits for diagnostic assays.

2 Claims, 8 Drawing Sheets

OTHER PUBLICATIONS

Volf, P. (1994) "Localization of the major immunogen and other glycoproteins of the louse *Polyplax spinulosa*" *International Journal for Parasitology* 24:1005-1010.

DATABASE EMBL Sequence Version Archive, Accession No. AZ549932, Nov. 15, 2000.

DATABASE EMBL-EBI, AC005507, Aug. 24, 1998.

DATABASE EMBL, Accession No. O93601, Nov. 1, 1998.

Figure 1

A. Molecular weight markers
B. Crude soluble antigen from whole *Bovicola ovis*
C. Crude soluble antigen from whole *Bovicola ovis* following removal of Bo1 by immunoaffinity chromatography
D. Bo1 purified by immunoaffinity chromatography
E. Molecular weight markers

Figure 2

Western blot of soluble *Bovicola ovis* antigen reacted with:

Lanes 25 to 28　monoclonal antibodies from second hybridoma clones of primary clone P6-B5
Lanes 29 to 32　monoclonal antibodies from second hybridoma clones of primary clone P6-D6
Molecular weight markers (kDa)
Lanes A　　　　normal mouse serum. Negative control
Lanes B　　　　hybridoma culture medium. Negative control
Lanes C　　　　serum from a mouse immunized with soluble *Bovicola ovis* faecal antigen. Positive control
Lanes D　　　　a known positive hybridoma culture supernatant. Positive control

Figure 3

```
PBAD18 vector-----------------------> ctttgctatgccatagcatttttatccataagattagcggatcctacctgacgc Arabinose promoter                                                                        Nde
tttttatcgcaactctctactgtttctccatacccgttttttttgggctagaaataatttttgtttaactttaagaaggagatatacatATGTCC
                                                                                          M  S CCAACAGAACTCGATCTTCGTCTTCTTGTTGAAACCGCTCGAGATATCTCTGTCATCTTGTTTAAAAACTTACATGCTGGATATAATGAAGTT
 P  T  E  L  D  L  R  L  L  V  E  T  A  R  D  I  S  V  I  L  F  K  N  L  H  A  G  Y  N  E  V AACCCCAAAATCGAAATACTGTTGAACGAATTGGCCCCCGAAGCTAAAGAAGGACTCCAAAAAATTATAAAAGAAATTAGAGATTTGGTCAAT
 N  P  K  I  E  I  L  L  N  E  L  A  P  E  A  K  E  G  L  Q  K  I  I  K  E  I  R  D  L  V  N GAAGAAGAAACCAGAATTAATGTCATCTTCAAAACTCTTATTGGTGCTTTGGACCAACTGAAACCAATTAAGGCACCATGCGCCGACCCCGTT
 E  E  E  T  R  I  N  V  I  F  K  T  L  I  G  A  L  D  Q  L  K  P  I  K  A  P  C  A  D  P  V TCTAAAGAAGCTAAAAAATTGGCCAACGATGTTGAAAGGGAAATCGTCAAATTCATTAAATATTTAGAACAAAAATACGAAAAGGTATTTACA
 S  K  E  A  K  K  L  A  N  D  V  E  R  E  I  V  K  F  I  K  Y  L  E  Q  K  Y  E  K  V  F  T AACATCAAGAATGGAGTTACCAAAGTAATCACCAGAGCCAGGAAATTGTTTGACACTGAAGTTCCCGAAGTCGTGAAATGTTTGACCCCCAAA
 N  I  K  N  G  V  T  K  V  I  T  R  A  R  K  L  F  D  T  E  V  P  E  V  V  K  C  L  T  P  K AACAAAGAGGCCACTAAATGCATCAATACACACATCGACAAAATTCTTGGTGAAGTTGCCCAAATCGGTGCCGACATTGGACTCCTTGTAATC
 N  K  E  A  T  K  C  I  N  T  H  I  D  K  I  L  G  E  V  A  Q  I  G  A  D  I  G  L  L  V  I TCTTCTGAAGAAGCTCTTAATCCCGTTATTAAGGAAGTTGTCGCCAAAATAGGTGAACAAGTGTTGAAGGTTTTGGGTGAAGGTAGGCCCATT
 S  S  E  E  A  L  N  P  V  I  K  E  V  V  A  K  I  G  E  Q  V  L  K  V  L  G  E  G  R  P  I Not 1    ---------------Etag---------------------
ATCAACAAAATCTCAGACTGTGTTGCAAAAATGgcggccgcaggtgcgccggtgccgtatccggatccgctggaaccgcgtgccgcggcacat
 I  N  K  I  S  D  C  V  A  K  M  a  a  a  g  a  p  v  p  y  p  d  p  l  e  p  r  a  a  h catcatcatcatcattagaattaattcgatctcggtacccggggatcctctagagtcgacctgcaggcatgcaagctt------> pBAD18
 h  h  h  h  h
```

Western blot of:

A. purified Bo1 reacted with Bo1 monoclonal antibody
B. purified recombinant Bo1 reacted with Bo1 monoclonal antibody
C. molecular weight markers
D. purified Bo1 reacted with PBS. Negative control
E. purified recombinant Bo1 reacted with PBS. Negative control Key: Aa – *Austrosimulium (Austrosimulium) australense*, Cp – *Culex pervigilans*;
An – *Aedes notoscriptus*; Bo – *Bovicola ovis*; Cs – *Calliphora stygia*; Cv – *Calliphora vicina*; Cr – *Chryomya rufifacies*; Ls – *Lucilia sericata*; Lc – *Lucilia cuprina*;
Dp – *Dermatophagoides pteronyssinus*.

Figure 8

Detection by ELISA of ovine IgE specific for crude B. ovis antigen and Bo1

SEQUENCE LISTING

<160> NUMBER OF SEQ ID NOS: 16

<210> SEQ ID NO 1
<211> LENGTH: 911
<212> TYPE: DNA
<213> ORGANISM: Bovicola ovis
<220> FEATURE:
<221> NAME/KEY: misc_feature
<222> LOCATION: (1)...(911)
<223> OTHER INFORMATION: n = A,T,C or G
<220> FEATURE:
<221> NAME/KEY: misc_feature
<222> LOCATION: 800, 875
<223> OTHER INFORMATION: n = A,T,C or G

<400> SEQUENCE: 1

```
atcaaaacaa caatgcaagg attaaaatta attttcgtcg ccttttttggc agttttcgct      60 gttgggtgtg agggaaatac tttggtcaaa tccccaacag aactcgatct tcgtcttctt     120
gttgaaaccg ctcgagatat ctctgtcatc ttgtttaaaa acttacatgc tggatataat     180
gaagttaacc ccaaaatcga aatactgttg aacgaattgg cccccgaagc taaagaagga     240
ctccaaaaaa ttataaaaga aattagagat ttggtcaatg aagaagaaac cagaattaat     300
gtcatcttca aaactcttat tggtgctttg gaccaactga aaccaattaa ggcaccatgc     360
gccgaccccg tttctaaaga agctaaaaaa ttggccaacg atgttgaaag ggaaatcgtc     420
aaattcatta aatatttaga acaaaaatac gaaaaggtat ttacaaacat caagaatgga     480
gttaccaaag taatcaccag agccaggaaa ttgtttgaca ctgaagttcc cgaagtcgtg     540
aaatgtttga cccccaaaaa caaagaggcc actaaatgca tcaatacaca catcgacaaa     600
attcttggtg aagttgccca aatcggtgcc gacattggac tccttgtaat ctcttctgaa     660
gaagctctta atcccgttat taaggaagtt gtcgccaaaa taggtgaaca agtgttgaag     720
gttttgggtg aaggtaggcc cattatcaac aaaatctcag actgtgttgc aaaaatgtaa     780
gaaataaaaa gaaataagtn aataaattaa ttttaatttt ttttttaattt tttttttctt     840 taatgccaaa caaaaaaatt aaaaattttt aaatnaattt taaaaattaa aaaaaaaaa      900 aaaaaaaaaa a                                                         911
```

<210> SEQ ID NO 2
<211> LENGTH: 254

```
<212> TYPE: PRT
<213> ORGANISM: Bovicola bovis

<400> SEQUENCE: 2
```

Met Gln Gly Leu Lys Leu Phe Val Ala Phe Leu Ala Val Phe Ala Val
 1               5                  10                  15

Gly Cys Glu Gly Asn Thr Leu Val Lys Ser Pro Thr Glu Leu Asp Leu
             20                  25                  30

Arg Leu Leu Val Glu Thr Ala Arg Asp Ile Ser Val Ile Leu Phe Lys
         35                  40                  45

Asn Leu His Ala Gly Tyr Asn Glu Val Asn Pro Lys Ile Glu Ile Leu
     50                  55                  60

Leu Asn Glu Leu Ala Pro Glu Ala Lys Glu Gly Leu Gln Lys Ile Ile
 65                  70                  75                  80

Lys Glu Ile Arg Asp Leu Val Asn Glu Glu Thr Arg Ile Asn Val
                 85                  90                  95

Ile Phe Lys Thr Leu Ile Gly Ala Leu Asp Gln Leu Lys Pro Ile Lys
                100                 105                 110

Ala Pro Cys Ala Asp Pro Val Ser Lys Glu Ala Lys Lys Leu Ala Asn
            115                 120                 125

Asp Val Glu Arg Glu Ile Val Lys Phe Ile Lys Tyr Leu Glu Gln Lys
        130                 135                 140

Tyr Glu Lys Val Phe Thr Asn Ile Lys Asn Gly Val Thr Lys Val Ile
145                 150                 155                 160

Thr Arg Ala Arg Lys Leu Phe Asp Thr Glu Val Pro Glu Val Val Lys
                165                 170                 175

Cys Leu Thr Pro Lys Asn Lys Glu Ala Thr Lys Cys Ile Asn Thr His
                180                 185                 190

Ile Asp Lys Ile Leu Gly Glu Val Ala Gln Ile Gly Ala Asp Ile Gly
            195                 200                 205

Leu Leu Val Ile Ser Ser Glu Glu Ala Leu Asn Pro Val Ile Lys Glu
        210                 215                 220

Val Val Ala Lys Ile Gly Glu Gln Val Leu Lys Val Leu Gly Glu Gly
225                 230                 235                 240

Arg Pro Ile Ile Asn Lys Ile Ser Asp Cys Val Ala Lys Met
                245                 250

```
<210> SEQ ID NO 3
<211> LENGTH: 30
<212> TYPE: PRT
<213> ORGANISM: Artificial Sequence
<220> FEATURE:
<223> OTHER INFORMATION: N-terminal aa sequence

<400> SEQUENCE: 3
```

Ser Pro Thr Glu Leu Asp Leu Arg Leu Leu Val Glu Thr Ala Arg Asp
 1               5                  10                  15

Ile Ser Val Ile Leu Phe Lys Asn Leu His Ala Gly Tyr Asn
             20                  25                  30

```
<210> SEQ ID NO 4
<211> LENGTH: 8
<212> TYPE: PRT
<213> ORGANISM: Artificial Sequence
<220> FEATURE:
<223> OTHER INFORMATION: artificially synthesized peptide

<400> SEQUENCE: 4
```

Asp Ile Ser Val Ile Leu Phe Lys
1               5

<210> SEQ ID NO 5
<211> LENGTH: 12
<212> TYPE: PRT
<213> ORGANISM: Artificial Sequence
<220> FEATURE:
<223> OTHER INFORMATION: artificially synthesized peptide

<400> SEQUENCE: 5

Asn Leu His Ala Gly Tyr Asn Glu Val Asn Pro Lys
1               5                   10

<210> SEQ ID NO 6
<211> LENGTH: 6
<212> TYPE: PRT
<213> ORGANISM: Artificial Sequence
<220> FEATURE:
<223> OTHER INFORMATION: artificially synthesized peptide

<400> SEQUENCE: 6

Val Phe Thr Asn Ile Lys
1               5

<210> SEQ ID NO 7
<211> LENGTH: 7
<212> TYPE: PRT
<213> ORGANISM: Artificial Sequence
<220> FEATURE:
<223> OTHER INFORMATION: artificially synthesized peptide

<400> SEQUENCE: 7

Ile Gly Glu Gln Val Leu Lys
1               5

<210> SEQ ID NO 8
<211> LENGTH: 6
<212> TYPE: PRT
<213> ORGANISM: Artificial Sequence
<220> FEATURE:
<223> OTHER INFORMATION: artificially synthesized peptide

<400> SEQUENCE: 8

Ile Asn Val Ile Phe Lys
1               5

<210> SEQ ID NO 9
<211> LENGTH: 12
<212> TYPE: PRT
<213> ORGANISM: Artificial Sequence
<220> FEATURE:
<223> OTHER INFORMATION: artificially synthesized peptide

<400> SEQUENCE: 9

Lys Leu Phe Asp Thr Glu Val Pro Glu Val Val Lys
1               5                   10

<210> SEQ ID NO 10
<211> LENGTH: 8
<212> TYPE: PRT
<213> ORGANISM: Artificial Sequence
<220> FEATURE:
<223> OTHER INFORMATION: artificially synthesized peptide

<400> SEQUENCE: 10

```
Asp Ile Ser Val Ile Leu Phe Lys
  1               5
```

<210> SEQ ID NO 11
<211> LENGTH: 13
<212> TYPE: PRT
<213> ORGANISM: Artificial Sequence
<220> FEATURE:
<223> OTHER INFORMATION: artificially synthesized peptide

<400> SEQUENCE: 11

```
Ile Glu Ile Leu Leu Asn Glu Leu Ala Pro Glu Ala Lys
  1               5                  10
```

<210> SEQ ID NO 12
<211> LENGTH: 10
<212> TYPE: PRT
<213> ORGANISM: Artificial Sequence
<220> FEATURE:
<223> OTHER INFORMATION: artificially synthesized peptide

<400> SEQUENCE: 12

```
Thr Leu Ile Gly Ala Leu Asp Gln Leu Lys
  1               5                  10
```

<210> SEQ ID NO 13
<211> LENGTH: 26
<212> TYPE: DNA
<213> ORGANISM: Artificial Sequence
<220> FEATURE:
<223> OTHER INFORMATION: BoP14-A oligonucleotide

<400> SEQUENCE: 13
catgctggat ataatgaagt waaycc                                   26

<210> SEQ ID NO 14
<211> LENGTH: 29
<212> TYPE: DNA
<213> ORGANISM: Artificial Sequence
<220> FEATURE:
<223> OTHER INFORMATION: BoP14-B oligonucleotide

<400> SEQUENCE: 14
ttaacaactt caggaacttc wgtrtcraa                                29

<210> SEQ ID NO 15
<211> LENGTH: 31
<212> TYPE: DNA
<213> ORGANISM: Artificial Sequence
<220> FEATURE:
<223> OTHER INFORMATION: Bo1-X2 primer

<400> SEQUENCE: 15
cttgcggccg ccattttttgc aacacagtct g                            31

<210> SEQ ID NO 16
<211> LENGTH: 32
<212> TYPE: DNA
<213> ORGANISM: Artificial Sequence
<220> FEATURE:
<223> OTHER INFORMATION: Bo1-X3 primer

<400> SEQUENCE: 16
cgcggatcca tatgtccccca acagaactcg at                           32

ALLERGEN AND TREATMENT

CROSS-REFERENCE TO RELATED APPLICATIONS

This is the U.S. National Phase under 35 U.S.C. § 371 of International Application No. PCT/NZ01/00065, filed Apr. 19, 2001, designating the United States and published in English, which claims priority to New Zealand Application No. 504096, filed Apr. 19, 2000.

TECHNICAL FIELD

The present invention concerns novel nucleoli sequences encoding a louse allergen, particularly although by no means exclusively from the chewing louse *Bovicola ovis*, and the use of said nucleoli sequences and protein allergen in the diagnosis, treatment and prevention of lice infestation and associated allergic disease.

BACKGROUND OF THE INVENTION

Lice are common ectoparasites of mammalian and avian species. The most important lice in domesticated animals are sucking lice (Insecta: *Phthiraptera: Trichodectidae: Anoplura*), which have mouthparts able to penetrate the skin of the host and enable the ingestion of tissue fluids and blood, and the chewing lice, (Insecta: *Phthiraptera: Trichodectidae: Mallophaga*), which predominantly ingest nutrients from the skin surface, hair, fur, wool or feathers. Chewing lice are common and economically important particularly on cattle, sheep, goats and equines and are also found on dogs, cats and birds including domesticated chickens.

*Bovicola ovis*, an example of a chewing louse, is a common external parasite of sheep world-wide. Infestation of sheep with this parasite has long been recognised as causing irritation of the skin with consequent rubbing and damage to the fleece (Johnson, Boray, Plant and Blunt, 1993; Lipson and Bacon-Hall, 1976). Discolouration, reduced yield and other undesirable qualities may occur in the fleeces of infested sheep (Kettle and Lukies, 1982; Kettle and Lukies, 1984; Cleland, Dobson and Meade, 1989). Additionally, recent work by the present inventors has shown that cockle, a serious defect of lambs' pelts recognised for more than 100 years (Seymour-Jones, 1913), is also associated with infestation of sheep with *B. ovis* (Heath, Cooper, Cole and Bishop, 1995; Heath, Cole, Bishop, Pfeffer, Cooper, and Risdon P, 1995). The inventors have further shown that cockle is characterized by a superficial perivascular dermatitis with features of an allergic response (Heath, Cole, Bishop, Pfeffer, Cooper, and Risdon P, 1995). Recent studies have supported the role of allergic immune responses to products of the louse in the development of cockle in sheep (Bany, Pfeffer, Phegan and Heath, 1995; Bany, Pfeffer and Phegan, 1995; Pfeffer, Phegan and Bany, 1997; Pfeffer, Bany, Phegan and Osborn, 1993). It can be expected that the allergic response to the louse contributes to the skin irritation that leads infested sheep to rub and damage their wool and to the skin lesions that severely devalue the pelts from affected lambs.

The economic consequences of *B. ovis* infestation of sheep is considerable when damage to wool and the costs of prevention of infestation are fully accounted (McLeod, 1995). To this can also be added the substantial cost of reduced quality of lambs pelts due to cockle. Apart from the direct economic costs, the continued use of conventional treatments to control louse infestation (synthetic insecticides and insect growth regulators) have detrimental effects through residues entering the environment and food chain as well as on farmer safety.

The consumer pressures to reduce the use of such harmful conventional treatments in the control of louse infestations and the development of resistance to some synthetic insecticides by lice necessitates refinement of current control strategies and a desire for new control methodologies and agents.

It is an object of the present invention to go some way towards achieving this desideratum or at least provide the public with a useful choice.

The present applicants have identified a louse antigen (allergen) that elicits an allergic response in affected sheep. The identified allergen, a protein designated Bo1, has been purified, amino acid sequenced, and the coding cDNA obtained and expressed in the bacterium, *Escherichia coli*. It is broadly to these allergens and their use in diagnosing, preventing and treating lice infestation and associated allergic diseases that the present invention is directed.

SUMMARY OF THE INVENTION

The subject invention concerns the identification, purification, sequencing, and production in recombinant or synthetic form of a novel protein allergen from chewing lice, including portions of said protein that contain at least one B cell or T cell epitope of the protein.

Accordingly, in one aspect, the present invention may broadly be said to consist in a substantially purified polypeptide which has the amino acid sequence of SEQ ID NO. 2, or a fragment or a variant thereof having substantially equivalent activity.

According to a further aspect there is provided a polypeptide substantially as described above wherein the polypeptide derived from a louse parasitic on an animal provokes a humoral and/or cellular immunological response in an animal infested by the louse, or a fragment or a variant thereof having substantially equivalent activity thereto.

More preferably the variant or fragment incorporates a B cell or T cell epitope of the polypeptide.

Thus it will be appreciated variants and fragments of the polypeptide of the invention which may be used to control louse infestation in animals and associated allergic diseases are also included in the present invention.

In general, the animals which may be infested by chewing lice include sheep, equines, cattle, dogs, cats or birds including chickens.

It is to be clearly understood that the invention also encompasses peptide analogues, which include but are not limited to the following:

1. Compounds in which one or more amino acids is replaced by its corresponding D-amino acid. The skilled person will be aware that retro-inverso amino acid sequences can be synthesised by standard methods; see for example Chorev and Goodman, 1993;
2. Peptidomimetic compounds, in which the peptide bond is replaced by a structure more resistant to metabolic degradation. See for example Olson et al, 1993; and
3. Compounds in which individual amino acids are replaced by analogous structures for example, gem-diaminoalkyl groups or alkylmalonyl groups, with or without modified termini or alkyl, acyl or amine substitutions to modify their charge.

The use of such alternative structures can provide significantly longer half-life in the body, since they are more resistant to breakdown under physiological conditions.

Methods for combinatorial synthesis of peptide analogues and for screening of peptides and peptide analogues are well known in the art (see for example Gallop et al, 1994; Hogan, 1997).

For the purposes of this specification, the term "peptide and peptide analogue" includes compounds made up of units which have an amino and carboxy terminus separated in a 1,2, 1,3, 1,4 or larger substitution pattern. This includes the 20 naturally-occurring or "common" α-amino acids, in either the L or D configuration, the biosynthetically-available or "uncommon" amino acids not usually found in proteins, such as 4-hydroxyproline, 5-hydroxylysine, citrulline and ornithine; synthetically-derived α-amino acids, such as α-methylalanine, norleucine, norvaline, Cα- and N-alkylated amino acids, homocysteine, and homoserine; and many others as known in the art.

It also includes compounds that have an amine and carboxyl functional group separated in a 1,3 or larger substitution pattern, such as β-alanine, γ-amino butyric acid, Freidinger lactam (Freidinger et al, 1982), the bicyclic dipeptide (BTD) (Freidinger et al, 1982; Nagai and Sato, 1985), amino-methyl benzoic acid (Smythe and von Itzstein, 1994), and others well known in the art. Statine-like isosteres, hydroxyethylene isosteres, reduced amide bond isosteres, thioamide isosteres, urea isosteres, carbamate isosteres, thioether isosteres, vinyl isosteres and other amide bond isosteres known to the art are also useful for the purposes of the invention.

A "common" amino acid is a L-amino acid selected from the group consisting of glycine, leucine, isoleucine, valine, alanine, phenylalanine, tyrosine, tryptophan, aspartate, asparagine, glutamate, glutamine, cysteine, methionine, arginine, lysine, proline, serine, threonine and histidine. These are referred to herein by their conventional three-letter or one-letter abbreviations.

An "uncommon" amino acid includes, but is not restricted to, one selected from the group consisting of D-amino acids, homo-amino acids, N-alkyl amino acids, dehydroamino acids, aromatic amino acids (other than phenylalanine, tyrosine and tryptophan), ortho-, meta- or para-aminobenzoic acid, ornithine, citrulline, norleucine, □-glutamic acid, aminobutyric acid (Abu), and α-α disubstituted amino acids.

The lice from which the polypeptide is derived belong to the suborder *Mallophaga* and preferably from the species *Bovicola ovis*, a chewing louse parasite on sheep.

Most preferably, the polypeptide comprises the allergen designated Bo1 from *B. ovis*.

Conveniently, the allergen polypeptide of the invention is obtained by expression of a DNA sequence coding therefore in a host cell or organism, or may be chemically synthesised.

In a further aspect, the present invention provides an isolated nucleic acid molecule encoding a polypeptide substantially as described above.

In a further aspect, the present invention provides an isolated nucleic acid molecule encoding a louse allergen polypeptide of the invention. Preferably the isolated nucleic acid molecule:

a) comprises a nucleoli sequence of SEQ ID NO. 1; or
b) is a functional fragment or variant of the molecule in (a); or
c) is able to hybridize under stringent conditions to the molecule in (a); or
d) is the complement of the molecule defined in (a), (b) or (c); or
e) is an anti-sense sequence corresponding to any of the sequences in (a)-(d).

This nucleic acid molecule may comprise a DNA, cDNA or RNA.

Preferably, the fragment or variant of the nucleic acid molecule above encodes a B cell or T cell epitope.

Also provided by the present invention are recombinant expression vectors which contain a DNA molecule of the invention, and hosts transformed with the vector of the invention capable of expressing a polypeptide of the invention.

An additional aspect of the present invention provides a ligand that binds to a polypeptide of the invention. Most usually, the ligand is an antibody or fragment of an antibody containing the binding domain. Most preferably the ligand is a monoclonal or polyclonal antibody which binds to the polypeptide of the invention or a functional fragment or variant thereof. In some other embodiments the ligand may be a phage display molecule.

In further aspects, the present invention provides a method for assaying samples for the presence of ligands which bind to Bo1 or a segment thereof comprising the steps of obtaining an excretion, secretion, tissue or blood sample from the host and exposing the sample to a Bo1 ligand binding agent or Bo1 probe via an ELISA or other suitable assay. When the ligand is an antibody, such assays indicate prior or present infestation by the ectoparasite of the host animal. When the ligand is an antibody of the IgE isotype, such assays are useful in diagnosis of hypersensitivity to the ectoparasite.

The present invention also provides a test kit suitable for use in an assay for ligands which bind to Bo1 or a segment thereof wherein the kit comprises a Bo1 ligand binding agent or probe incorporated into an ELISA or other suitable assay.

The present invention also provides an alternative method of diagnosing hypersensitivity to the louse in a host (and thus prior or present infestation of the host by the louse) via intradermal skin testing. In this method a polypeptide of the invention or fragment or variant thereof injected intradermally into the host will elicit a characteristic response in the skin of hypersensitive hosts in contrast to little or no response in non-sensitised hosts. In vitro correlates of this method would include exposing isolated tissues or cells of the host to a polypeptide of the invention as defined above and measuring immunologically mediated stimulation of the tissues or cells, for example, release of histamine from blood basophils or proliferation or transformation of lymphocytes. Use of a polypeptide of the invention as defined herein would increase the specificity of such methods as to the ectoparasite provoking such immunological sensitisation of the host compared to published methods where crude antigen preparations were used (Pfeffer, Phegan and Bany (1997;); Bany, Pfeffer and Phegan (1995); Bany, Pfeffer, Phegan and Heath (1995).

The present invention also provides a vaccine to prevent or reduce Bo1 hypersensitivity in susceptible animals wherein the vaccine includes an agent selected from the group comprising:

a) a polypeptide according to the present invention substantially as described above;
b) a nucleic acid molecule according to the present invention; substantially as described above
c) organisms transfected with and/or expressing the DNA or RNA for the polypeptide according to (a);
d) ligands or probes which bind to the polypeptide according to (a).

The present invention further provides a composition including an effective amount of an agent selected from the group comprising:
   a) the nucleic acid molecule according to the present invention substantially as described above;
   b) the polypeptide according to the present invention substantially as described above;
   c) organisms transfected with and/or expressing the DNA or RNA for the polypeptide according to (b); or
   d) ligands or probes which bind to the polypeptide according to (b); together with a pharmaceutically or veterinarily suitable carrier or diluent.

According to yet a further aspect of the present invention there is provided a method of diagnosing ectoparasite infestation comprising the steps of:
   a) obtaining an excretion, secretion, , tissue or blood sample from the host; and
   b) exposing the sample to a ligand or probe for an identified antigen present in the ectoparasite's faeces via an ELISA or other suitable assay.

The present invention provides test kits for diagnosing ectoparasite infestation. In one aspect the test kit may include a ligand or probe for an identified antigen present in the ectoparasite's faeces incorporated into an ELISA or other suitable assay.

In preferred embodiments the ectoparasite may be *B. ovis* and the identified allergen may be Bo1. Although the above are preferred embodiments they should not be seen as limiting the scope of this aspect of the present invention which may be utilised for a wide range of ectoparasites.

The invention also encompasses methods of treating animals, or preventing animals from, exhibiting allergic hypersensitivity to the Bo1 polypeptide comprising the step of administering an effective amount of a vaccine or a composition substantially as described above.

According to a yet a still further aspect of the present invention there is provided a method of diagnosing in an animal hypersensitivity to *Bovicola ovis* or the Bo1 polypeptide comprising the steps
   a) injecting intradermally a suitable amount of the polypeptide as claimed in claims 1-8 together with a pharmaceutically or veterinarily suitable carrier or diluent;
   b) at appropriate times thereafter examining the site of injection to detect the nature of the reaction to the polypeptide of the invention
   c) determining on the basis of these observations in comparison to those on injections of carrier or diluent alone and other control solutions whether a specific reaction to the polypeptide of the invention was evident While the invention is broadly as defined above, it will be appreciated by those persons skilled in the art that it is not limited thereto and that it also includes embodiments of which the following description gives examples.

Methods and pharmaceutical carriers for preparation of pharmaceutical compositions are well known in the art, as set out in textbooks such as Remington's Pharmaceutical Sciences, 19th Edition, Mack Publishing Company, Easton, Pa., USA.

The compounds, vaccines and compositions of the invention may be administered by any suitable route, and the person skilled in the art will readily be able to determine the most suitable route and dose for the condition to be treated. Dosage will be at the discretion of the attendant physician or veterinarian, and will depend on the nature and state of the condition to be treated, the age and general state of health of the subject to be treated, the route of administration, and any previous treatment which may have been administered.

The carrier or diluent, and other excipients, will depend on the route of administration, and again the person skilled in the art will readily be able to determine the most suitable formulation for each particular case.

For the purposes of this specification it will be clearly understood that the word "comprising" means "including but not limited to", and that the word "comprises" has a corresponding meaning.

BRIEF DESCRIPTION OF DRAWINGS

In particular, preferred aspects of the invention will be described in relation to the accompanying drawings in which:

FIG. 1 shows a photograph of a silver stained 12% polyacrylamide gel showing protein bands contained in the indicated preparations from the louse, *Bovicola ovis*. Note bands at approximately 28.5, 42 and 83 kDa in lane D;

FIG. 2 shows a photograph of a Western blot of soluble *Bovicola ovis* antigen reacted with monoclonal antibodies from hybridomas derived from a mouse immunised with soluble *Bovicola ovis* faecal antigen. Note major band at approximately 28.5 kDa and minor bands at approximately 83 kDa (lanes 30 to 32, C and D) and at approximately 14 kDa (lanes 27 and 28);

FIG. 3 shows a diagrammatic representation of the strategy used to clone the coding sequence for the mature Bo1 protein into the AY2-4 vector;

FIG. 8. shows the results of an ELISA to detect ovine IgE specific for crude *Bovicola ovis* antigen and purified Bo1 protein.

BRIEF DESCRIPTION OF SEQUENCES

Figure 4:
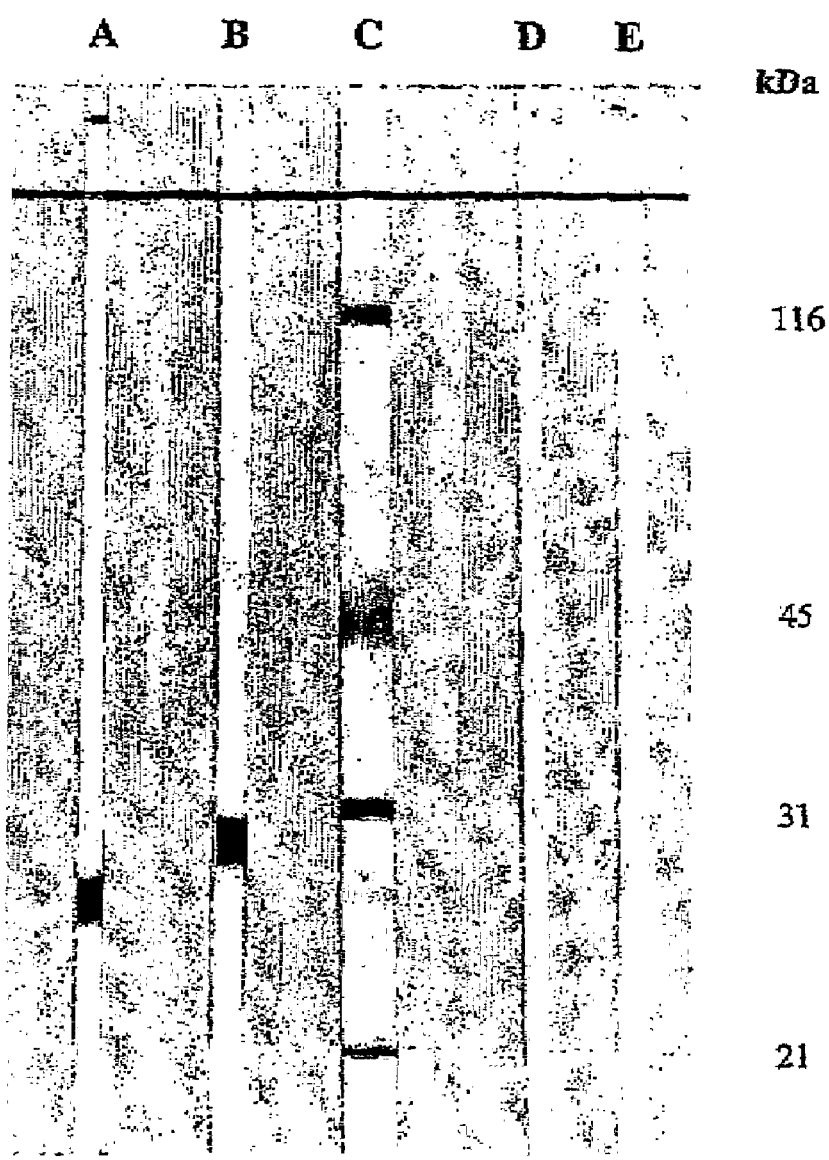
FIG. 4 shows a photograph of a Western blot of purified native and recombinant Bo1 reacted with a Bo1 monoclonal antibody. Note the apparent higher molecular weight of the recombinant compared to the native Bo1.

SEQ ID NO. 1 is the nucleoli sequence of the coding DNA of the complete Bo1 protein.

SEQ ID NO. 2 is the amino acid sequence of the complete Bo1 protein.

DETAILED DESCRIPTION OF THE INVENTION

The present applicants have shown for the first time that *Bovicola ovis*-infested sheep mount immunological responses to the infesting louse. Evidence of these responses was seen using crude preparations of soluble allergens of the invention isolated from whole lice and from louse faecal preparations.

The present invention provides a substantially purified louse polypeptide allergen which has the amino acid sequence of SEQ ID NO: 2 or a fragment or variant thereof having substantially equivalent activity thereto. Preferably the polypeptide provokes a humoral and/or cellular immunological response in an animal infested by the louse, or is a fragment or variant thereof having substantially equivalent activity thereto.

The term "substantially purified" means substantially isolated or separated away from contaminating proteins or peptides or other material in the cell or organism in which the polypeptide naturally occurs and includes polypeptides purified by standard purification techniques as well as polypeptides prepared by recombinant technology and those chemically synthesised. Preferably the polypeptide is purified from whole lice or lice faecal preparations.

The term "variant" as used herein refers to nucleoli and polypeptide sequences wherein the nucleoli or amino acid sequence exhibits substantially 60% or greater homology with the nucleoli or amino acid sequence of the Figures, preferably 75% homology and most preferably 90-95% homology to the sequences of the present invention—as assessed by GAP or BESTFIT (nucleotides and peptides), or BLASTP (peptides) or BLAST X (nucleotides). The variant may result from modification of the native nucleoli or amino acid sequence by such modifications as insertion, substitution or deletion of one or more nucleotides or amino acids or it may be a naturally-occurring variant. The term "variant" also includes homologous sequences which hybridise to the sequences of the invention under standard hybridisation conditions defined as 2×SSC at 65° C., or preferably under stringent hybridisation conditions defined as 6×SCC at 55° C. Where such a variant is desired, the nucleoli sequence of the native DNA is altered appropriately. This alteration can be effected by synthesis of the DNA or by modification of the native DNA, for example, by site-specific or cassette mutagenesis. Preferably, where portions of cDNA or genomic DNA require sequence modifications, site-specific primer directed mutagenesis is employed, using techniques standard in the art.

The term "ligand" refers to any molecule which may bind to another molecule such as a polypeptide or peptide and should be taken to include, but not be limited to, antibodies and phage display molecules.

The term "tissue" refers to any coherent collection of specialised cells and shall be taken to include, but not be limited to: skin, fur, hair, wool and feathers.

The reader will appreciate that mimetics of the polypeptides of the invention which have substantially identical function as the polypeptide of the invention are also included within the scope of the present invention. The production of such mimetics is within the capabilities of a skilled worker in the art.

The polypeptides of the invention can be prepared in a variety of ways. For example, they can be produced by isolation from a natural source, by synthesis using any suitable known techniques (such as by stepwise, solid phase, synthesis described by Merryfield (1963), *J. Amer. Chem. Soc.* Vol 85:2149-2156) or as preferred, through employing DNA techniques.

The variants of the polypeptides can similarly be made by any of those techniques known in the art. For example, variants can be prepared by site-specific mutagenesis of the DNA encoding the native amino acid sequence as described by Adelman et al. DNA 2:183 (1983).

In addition, polypeptides having substantial identity to the amino acid sequences of the invention can also be employed in preferred embodiments. Here "substantial identity" means that two sequences, when optimally aligned such as by the programs GAP or BESTFIT using default gap weights, or as measured by computer algorithm BLASTP, share at least 60%, preferably 75%, and most preferably 90-95% sequence identity. Preferably, residue positions which are not identical differ by conservative amino acid substitutions. For example, the substitution of amino acids having similar chemical properties such as charge or polarity are not likely to affect the properties of a protein. Examples include glutamine for asparagine or glutamic acid for aspartic acid.

Where it is preferred, recombinant techniques may be used to produce the polypeptide of the invention, the first step is to obtain DNA encoding the desired product. Such DNA comprises a still further aspect of this invention. The DNA of the invention may encode a native or modified polypeptide of the invention or an active fragment or variant thereof.

Preferably, the DNA comprises an isolated nucleic acid molecule encoding a louse allergenic polypeptide of the invention, and more preferably, the nucleic acid molecule comprises the nucleoli sequence of SEQ ID NO: 1 or a functional fragment or variant thereof.

The term "isolated" means substantially separated or purified away from contaminating sequences in the cell or organism in which the nucleic acid naturally occurs and includes nucleic acids purified by standard purification techniques as well as nucleic acids prepared by recombinant technology, including PCR technology, and those chemically synthesised. Preferably, the nucleic acid molecule is derived from genomic DNA or the mRNA of the *Bovicola ovis* chewing louse.

The DNA can be isolated from any appropriate natural source or can be produced as intron free cDNA using conventional techniques. DNA can also be produced in the form of synthetic oligonucleotides where the size of the active fragments to be produced permits. By way of example, the Triester method of Matteucci et al *J. Am. Chem. Soc.* Vol 103:3185-3191 (1981) may be employed.

Where desirable, the DNA of the invention can also code for a fusion protein comprising the polypeptide of the invention and a carrier protein. This carrier protein will generally be cleavable from the polypeptide, fragment or variant thereof under controlled conditions. Examples of commonly employed carrier proteins are βgalactosidase and glutathione-S-transferase.

As indicated above, also possible are variants of the polypeptide which differ from the native amino acid sequence by insertion, substitution or deletion of one or more amino acids. Where such a variant is desired, the nucleoli sequence of the native DNA is altered appropriately. This alteration can be made through elective synthesis of the DNA or by modification of the native DNA by, for example, site-specific or cassette mutagenesis. Preferably, where portions of cDNA or genomic DNA require sequence modifications, site-specific primer directed mutagenesis is employed using techniques standard in the art.

Most preferably, the invention relates to a protein allergen from *Bovicola ovis*, a chewing louse parasitic on sheep. It will be recognised by those skilled in the art that nucleoli polymorphism may occur in the coding DNA and amino acid polymorphism may occur in the protein. Additionally it will be recognised by those skilled in the art that the same or substantially similar proteins can be expected to occur in other chewing lice (Suborder *Mallophaga*). Such proteins can be advantageously used in applications as shown for the protein from *B. ovis*. All such sequence variations in coding DNA and amino acids of the protein, or portion thereof, are within the scope of the invention.

In a further aspect, the present invention consists in replicable transfer vectors suitable for use in preparing a polypeptide or peptide of the invention. These vectors may be constructed according to techniques well known in the art, or may be selected from cloning vectors available in the art.

The cloning vector may be selected according to the host or host cell to be used. Useful vectors will generally have the following characteristics:
  (a) the ability to self-replicate;
  (b) the possession of a single target for any particular restriction endonuclease; and
  (c) desirably, carry genes for a readily selectable marker such as antibiotic resistance.

Two major types of vector possessing these characteristics are plasmids and bacterial viruses (bacteriophages or phages). Presently preferred vectors include the bacteriophage lambda Uni-ZAP™ XR and the modified plasmid pBAD18 vector, AY2-4 (see FIG. 3 and Guzman, L., Belin, D., Carson, M. J. and Beckwith, J. (1995). Tight regulation, modulation, and high-level expression by vectors containing the arabinose PBAD promoter. *J. Bacteriol*. 177:4121-4130).

The DNA molecules of the invention may be expressed by placing them in operable linkage with suitable control sequences in a replicable expression vector. Control sequences may include origins of replication, a promoter, enhancer and transcriptional terminator sequences amongst others. The selection of the control sequence to be included in the expression vector is dependent on the type of host or host cell intended to be used for expressing the DNA.

Generally, eucaryotic, yeast, insect or mammalian cells are useful hosts. Also included within the term hosts are plasmid vectors. Suitable procaryotic hosts include *E. coli, Bacillus* species and various species of *Pseudomonas*. Commonly used promoters such as β-lactamase (penicillinase) and lactose (lac) promoter systems are all well known in the art. Any available promoter system compatible with the host of choice can be used. Vectors used in yeast are also available and well known. A suitable example is the 2 micron origin of replication plasmid.

Similarly, vectors for use in mammalian cells are also well known. Such vectors include well known derivatives of SV-40, adenovirus, retrovirus-derived DNA sequences, Herpes simplex viruses, and vectors derived from a combination of plasmid and phage DNA.

Further eucaryotic expression vectors are known in the art (e.g. P. J. Southern and P. Berg, *J. Mol. Appl. Genet*. 1327-341 (1982); S. Subramani et al., *Mol. Cell. Biol*. 1, 854-864 (1981); R. J. Kaufmann and P. A. Sharp, "Amplification and Expression of Sequences Cotransfected with a Modular Dihydrofolate Reducase Complementary DNA Gene, *J. Mol. Biol*. 159, 601-621 (1982); R J. Kaufmann and P. A. Sharp, *Mol. Cell. Biol*. 159, 601-664 (1982); S. I. Scahill et al., "Expressions And Characterization Of The Product Of A Human Immune Interferon DNA Gene In Chinese Hamster Ovary Cells," *Proc. Natl. Acad. Sci. USA*. 80, 4654-4659 (1983); G. Urlaub and L. A. Chasin, *Proc. Natl. Acad. Sci. USA*. 77, 4216-4220, (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the glycolytic promoters of yeast acid phosphatase, e.g. Pho5, the promoters of the yeast alpha-mating factors, and promoters derived from polyoma, adenovirus, retrovirus, and simian virus, e.g. the early and late promoters of SV40, and other sequences known to control the expression of genes of prokaryotic and eucaryotic cells and their viruses or combinations thereof.

A preferred promoter for use herein is the Arabinose promoter (Guzman, L., Belin, D., Carson, M. J. and Beckwith, J.,1995. ), however, any suitable promoter is included within the scope of the present invention as would be appreciated by a skilled worker.

In the construction of a vector it is also an advantage to be able to distinguish the vector incorporating the foreign DNA from unmodified vectors by a convenient and rapid assay. Reporter systems useful in such assays include reporter genes, and other detectable labels which produce measurable colour changes, antibiotic resistance and the like. In one preferred vector, the β-galactosidase reporter gene is used, which gene is detectable by clones exhibiting a blue phenotype on X-gal plates. This facilitates selection. In one embodiment, the β-galactosidase gene may be replaced by a polyhedrin-encoding gene; which gene is detectable by clones exhibiting a white phenotype when stained with X-gal. This blue-white color selection can serve as a useful marker for detecting recombinant vectors.

Once selected, the vectors may be isolated from the culture using routine procedures such as freeze-thaw extraction followed by purification.

For expression, vectors containing the DNA of the invention to be expressed and control signals are inserted or transformed into a host or host cell. Some useful expression host cells include well-known prokaryotic and eucaryotic cells. Some suitable prokaryotic hosts include, for example, *E. coli*, such as *E. coli* S G-936, *E. coli* HB 101, *E. coli* W3110, *E. coli* X1776, *E. coli* X2282, *E. coli* DHT, and *E. coli*, MR01, *Pseudomonas, Bacillus*, such as *Bacillus subtilis*, and *Streptomyces*. Suitable eucaryotic cells include yeast and other fungi, insect, animal cells, such as COS cells and CHO cells, human cells and plant cells in tissue culture.

Depending on the host used, transformation is performed according to standard techniques appropriate to such cells. For prokaryotes or other cells that contain substantial cell walls, the calcium treatment process (Cohen, S N *Proc Nat Acad Sci, USA* 69 2110 (1972)) may be employed. For mammalian cells without such cell walls the calcium phosphate precipitation method of Graeme and Van Der Eb, *Virology* 52:546 (1978) is preferred. Transformations into plants may be carried out using *Agrobacterium tumefaciens* (Shaw et al., Gene 23:315 (1983) or into yeast according to the method of Van Solingen et al. J. Bact. 130: 946 (1977) and Hsiao et al. *Proc Nat Acad Sci, USA* 76:3829 (1979).

Upon transformation of the selected host with an appropriate vector the polypeptide encoded can be produced, often in the form of fusion protein, by culturing the host cells. The polypeptide of the invention may be detected by rapid assays as indicated above. The polypeptide is then recovered and purified as necessary. Recovery and purification can be achieved using any of those procedures known in the art, for example by absorption onto and elution from an anion exchange resin. This method of producing a polypeptide of the invention constitutes a further aspect of the present invention.

Host cells transformed with the vectors of the invention also form a further aspect of the present invention.

In a further aspect, the present invention provides a ligand that binds to a polypeptide of the invention.

In one embodiment the ligand may be an antibody or antibody fragment raised against the polypeptide of the invention. Such antibodies may be polyclonal, but are preferably monoclonal.

Polyclonal antibodies may be produced according to the method used by Koelle el al.; *Cell* 67:59-77, 1991 incorporated herein by reference. Useful antibody production protocols are outlined in U.S. Pat. No. 5,514,578 incorporated herein by reference. Monoclonal antibodies may be produced by methods known in the art. These methods include the immunological method described by Kohler and Milstein in *Nature* 256:495-497 (1975) as well as by the recombinant DNA method described by Huse et al. *Science* 246:1275-1281 (1989). Any of the assay methods detailed in U.S. Pat. No. 5,514,578 are also incorporated for use herein by reference.

An understanding of the tertiary structure and spatial interactions between the Bo1 allergen (especially ligand-binding domains) and its ligand will provide ways to select highly specific ligands which may be bound only by a modification of a natural receptor ligand-binding domain. Also, this knowledge will provide directions for new designs using the combination of Bo1 allergens with ligands and methods to design and select peptide mimetics of ligands with high specificity by techniques such as phage differential display.

In another embodiment the ligand may comprise molecules that bind to the polypeptide of the invention which are derived from natural sources, including plants, animals and insects. Insect extracts which produce mimetics of the Bo1 allergen are of particular interest.

Accordingly, in a further aspect, the present invention provides a method of assaying samples for the presence of ligands. Assaying processes using polypeptides as a ligand binding agent or probe are well within the capacity of the art skilled worker. The selection of the segment to be used as a probe will allow particular functionally associated segments to be isolated. For example, if a segment of the polypeptide binding domain of the present invention is used as a probe, identical or similar polypeptide binding domains can be identified, isolated and the encoding DNA determined.

It will also be appreciated that the selection of probes highly specific for *Bovicola ovis*, will provide an opportunity to assay samples in a rapid and highly specific manner to detect the presence of *Bovicola ovis*.

Samples of material to be screened may be prepared in the form of substrate solutions, then exposed to the ligand binding agent or probe. The presence of a ligand binding agent/ligand complex may be detected according to methods also known in the art. Examples of such methods include agglutination, radioimmunoassay, fluorescence or enzyme immunoassay techniques. A suitable screening test is an ELISA assay. In this method of the invention it is presently preferred that the Bo1 binding domain be used as the ligand binding agent.

In a further aspect the present invention provides test kits suitable for use in such assays. An example of such a test kit is an ELISA assay test kit including a ligand binding agent of the invention.

In a further aspect, the present invention provides a method of assaying samples for the presence of polypeptides or fragments or variants thereof or other antigenic molecules excreted in the faeces of ectoparasites that are specific for individual species or related groups of ectoparasites. Examples of such methods include agglutination, radioimmunoassay, fluorescence or enzyme immunoassay techniques. A suitable screening test is an ELISA assay including a ligand (or ligands) that binds to an identified antigenic molecule in the faeces of the ectoparasite. Such assays will enable convenient and rapid screening of multiple samples from hosts for the detection of infestation of the host by ectoparasites.

In this method of the invention it is presently preferred that monoclonal antibody be used as the ligand to detect ectoparasite infestation.

In a further aspect the present invention provides test kits suitable for use in such assays. An example of such a test kit is an ELISA assay test kit including a ligand of the invention.

A further aspect of the present invention provides a method of diagnosing hypersensitivity to the louse in a host (and thus prior or present infestation of the host by the louse) via intradermal skin testing. In this method a polypeptide of the invention or fragment or variant thereof injected intradermally into the host will elicit a characteristic specific response in the skin of hypersensitive hosts in contrast to little or no response in non-sensitised hosts. The response in the hypersensitive host will include a least one of the following responses at the site of injection; wheal, flare, induration. This use of intradermal skin testing employing injection of an allergen preparation together with injection of a negative control preparation and histamine at adjacent skin sites is well known to those skilled in the art. In vitro correlates of this method will also be appreciated by those skilled in the art and include exposing isolated tissues or cells of the host to a polypeptide of the invention as defined above and measuring immunologically mediated stimulation of the tissues or cells, for example, release of histamine from blood basophils or proliferation or transformation of lymphocytes. Use of a polypeptide of the invention as defined herein would increase the specificity of such methods for immunological sensitisation of the host by *Bovicola ovis* compared to published methods where crude antigen preparations were used (Pfeffer, Phegan and Bany (1997;); Bany, Pfeffer and Phegan (1995); Bany, Pfeffer, Phegan and Heath (1995).

Diagnostic assays or tests employing the protein, peptides and/or specific antibodies or synthetic molecules that mimic these embodiments are considered to be part of this invention and may be useful firstly, to identify infestation with the chewing lice in animals, and secondly, to identify hypersensitivity in infested animals in vivo or in vitro.

Further it will be obvious to those skilled in the art, that the subject polypeptides, peptides and antibodies or other molecules that specifically bind or mimic the subject protein and peptides and antibodies may be used as novel agents to control infestation by chewing lice or to prevent or suppress the immunological hypersensitivity arising as a consequence of such infestation and are, as such, included in the scope of the present invention. Firstly, the protein or peptides in native form or modified, the total coding DNA of the protein or part thereof, recombinants incorporating all or part of the protein, organisms transfected with and/or expressing the coding DNA or RNA for the protein or peptides, and synthetic molecules that copy or mimic the protein or peptides may be formulated into vaccines to elicit protective immunity in the host to the chewing louse. Further, antibodies specific to epitopes of the protein or peptides of the invention, or synthetic molecules mimicking these antibodies may be used to passively immunize the host so that the host is partially or completely protected from infestation with the louse. Secondly, the protein or peptides in native or modified forms, organisms transfected with and/or expressing the coding DNA or RNA for the protein or peptides, or specific monoclonal or polyclonal antibodies or synthetic molecules that mimic the specific antibodies may be used to damage the chewing lice or interfer with physiological processes of the chewing lice. Thirdly, it will be obvious that the protein or peptides in native form or modified, the total coding DNA of the protein or part thereof, and recombinants incorporating the protein or peptides, organisms transfected with and/or expressing the coding DNA or RNA for the protein or peptides, and synthetic molecules that mimic the protein, peptides or specific antibodies may be formulated into treatments to prevent, ameliorate or reverse the allergic hypersensitivity that develops in the host animal in response to infestation by the chewing louse. It is intended that these applications also be included in this patent.

The protein or peptides of the invention may be formulated into vaccines which when administered to animals may elicit a protective response against the louse. Alternatively, a polynucleotide molecule of the invention may be incorporated into a vector or plasmid or transformed into a host which when administered to the animal may also elicit a protective response against the louse. It is also possible that the antibodies, fragments of antibodies, phage display molecules, or transformed hosts containing or secreting such molecules may be systemically administered to an animal and thereby provide passive protection. The Bo1 protein may be required for functions important for the viability or fecundity of the louse and thus the invention may be used to interfere with this function and thereby prevent or control infestations by the louse. Synthetic or recombinant molecules which block the function of the protein or disrupt regulation of production of the protein in the louse may be designed from knowledge of the sequences of the invention, synthetised and advantageously applied to animals. The hypersensitivity elicited by infestations of the louse may be prevented or reduced by administering the protein, peptides, polynucleotide molecules or transformed hosts of the invention to susceptible animals in regimens that prevent the development of or downregulate the immunological responses leading to hypersensitivity disease. Examples of such regimens may include variations of route of administration and coadministration with various adjuvants, cytokines or organisms. The present invention may also be used to define B and T cell epitopes of the Bo1 protein important in the hypersensitivity elicited in the host animal. This may be done by synthetising overlapping peptides and determining recognition of the individual peptides by antibodies or T cells from hypersensitive hosts. Such defined epitopes may be used in preventing or controlling the hypersensitivity. For example, peptides containing epitopes of the protein of the invention may be used in desensitisation regimens of animal hosts without the danger of cross-linking IgE on mast cells and thereby eliciting anaphylaxis. The uses described herein are intended to be encompassed by the present invention.

Non-limiting examples illustrating the invention will now be provided.

It will be appreciated that the above description is provided by way of example only and variations in both the materials and techniques used which are known to those persons skilled in the art are contemplated.

PROTOCOL

EXAMPLE 1

Preparation of Soluble Antigen from Whole Lice and Louse Faeces

Live nymph and adult *Bovicola ovis* were collected from infested sheep and separated from wool and any other debris in a glass petri dish by raising one side of the dish and allowing the lice to migrate to the lower side. The lice were then placed in a ceramic mortar and snap frozen by adding liquid nitrogen. While maintaining the mortar over liquid nitrogen, the lice were crushed to a fine powder with a pestle. The powder was then allowed to thaw briefly and cold phosphate buffered saline containing 1 mM Pefabloc® (Boehringer Mannheim) was added at the rate of 10 ml per gram of lice. The preparation was transferred to a glass homogeniser maintained over ice and homogenised. The preparation was ultracentrifuged (10 000 g, 20 min, 4° C.) to remove particulate matter. The supernatant containing the soluble antigen was filtered through sterile 0.2 µm filters. For short-term storage, the supernatant was held at 4° C. For long-term storage, the supernatant was mixed 1 to 1 by volume with glycerol (AnalaR®, BDH) and stored at −20° C. Typically the protein concentrations of the supernatants following mixing with glycerol were 2 to 3 mg per ml when measured using the BCA Protein Assay (Pierce) after precipitation with 5% trichloroacetic acid. The complex nature of the crude soluble antigen prepared from whole lice is shown in FIG. 1.

To obtain louse faeces, lice separated from wool and debris were maintained overnight in clean glass petri dishes under conditions of controlled temperature and relative humidity according to the method of Hoplins, 1970. In vitro colonization of the sheep biting louse, *Bovicola ovis*. (Annals of the Entomological Society of America. 63:1196-1197). Lice were then poured off the plate and any dead lice, parts of lice or other debris attached to the surface of the plate removed. The faecal pellets attached to the glass plate were suspended in 10 ml phosphate buffered saline containing 1 mM Pefabloc® and transferred to a glass homogeniser maintained over ice and homogenised. This preparation was then ultracentrifuged and filtered as above and stored at 4° C. Protein levels in soluble louse faecal antigen preparations were measured by absorbance at 280 nm or by the BCA Protein Assay (Pierce).

EXAMPLE 2

Isolation of Ovine IgE and Coupling to Affinity Columns

Sera collected from sheep infested with *B. ovis* were screened by ELISA to identify those with higher levels of IgE binding with whole louse soluble antigen. A selected serum was then diluted 1 to 5 by volume with wash buffer (50 mM phosphate buffer, 500 mM NaCl buffer, pH 7.0) and filtered through a 0.2 µm filter. The IgE in the diluted serum was separated using an immunoaffinity column constructed by coupling a monoclonal antibody specific for ovine IgE to a HiTrap NHS-activated column (Pharmacia Biotech) as described by Shaw, R. J., Grimmett, D. J., Donaghy, M. J., Gatehouse, T. K., Shirer, C. L. and Douch, P. G. C. 1996. Production and characterisation of monoclonal antibodies recognising ovine IgE. *Veterinary Immunology and Immunopathology*. 51:235-251. The eluates from the IgE specific affinity column were dialysed against wash buffer and further purified by passing the preparation over affinity columns to which were coupled an irrelevant monoclonal antibody or protein G. Analysis of the resultant preparations by SDS PAGE under reducing conditions showed bands typical of IgE heavy and light chain at high (>90%) levels of purity. Approximately 10 mg of ovine IgE were coupled to 1 ml HiTrap NHS-activated columns (Pharmacia Biotech) as per the manufacturer's recommendations.

EXAMPLE 3

Isolation of Native Allergens from *Bovicola ovis* Using Ovine-IgE Immunoaffinity Chromatography Crude soluble *B. ovis* and *B. ovis* faecal antigen preparations were prepared as in Example 1 except that the diluent was wash buffer (50 mM phosphate buffer, 500 mM NaCl buffer, pH 7.0). The diluted antigen preparations were loaded onto an ovine IgE immunoaffinity column constructed as in Example 2. The column was then washed with wash buffer, and the native allergens were eluted with 100 mM glycine at pH 3.0. The eluates were returned to neutral pH by adding 1 M Tris, 1.5 M NaCl, pH 8.0 at a ratio of 1 to 10 (v/v). The allergen eluates were concentrated by ultrafiltration (MicrosepTM Centrifugal Concentrators, Pall Filtron Corporation, cutoff 3000 kD) and examined by SDS-PAGE under reducing conditions. Intradermal skin testing confirmed that the eluates from the whole louse and the louse faeces antigen preparations contained allergens.

EXAMPLE 4

Preparation of Monoclonal Antibody

BALB/c mice were injected subcutaneously with louse faecal antigen preparation (up to 1 mg total protein) mixed 1 to 1 with Freund's Complete Adjuvant and boosted intraperitoneally with similar amounts of louse faecal antigen in Freund's Incomplete Adjuvant on 2 occasions. Mice showing robust antibody responses were identified by assaying serum samples from the mice in ELISA for reactivity with louse faecal antigen. Spleen lymphocytes from selected mice were fused with NS-1 myeloma cells by standard techniques. The resultant hybridomas were plated out in 1 ml cultures over 5, 24 well plates in selective media conditioned with BALB/c thymocytes. Subsequently, the media in the wells was screened by ELISA for murine IgG antibody recognizing soluble faecal antigen. The hybridomas from positive wells were subjected to limiting dilution in 96 well culture plates at mean concentrations of 0.5, 1 and 2 cells per well. These hybridomas were again screened for antibody recognizing crude soluble louse faecal antigen. Clones producing antibody to faecal antigen were also screened by ELISA to determine reactivity of the antibody with isolated native allergens prepared as described in Example 3. Single hybridomas identified as producing antibody to native allergens were cloned a second time by limiting dilution. Hybridomas from the second cloning were expanded and cryopreserved. Monoclonal antibodies selected for further use were of the murine IgG-1 isotype. For the production of monoconal antibody, cloned hybridomas were expanded by standard culture techniques, allowed to overgrow and the supernatant collected.

Monoclonal antibodies produced by the hybridomas recognised an immunodominant molecule with a major moiety of 28.5 kDa rMW on Western blots of crude louse or louse faecal antigen (FIG. 2). This corresponded to one of the major bands observed on SDS PAGE of putative native allergens obtained by IgE affinity chromatography of both whole louse and louse faecal antigen preparations. Minor bands were also observed at approximately 14, 42, and 83 kDa rMW. The higher rMW moieties appear to represent multiples of the 14 kDa band, that is, 2×14=28 (~28.5), 3×14=42 and 6×14=84 (~83).

The protein identified by the monoclonal antibodies was designated Bo1.

EXAMPLE 5

Purification of Bo1 Allergen

Monoclonal antibody prepared as described in Example 4 was purified over a Protein G affinity chromatography column and coupled to a HiTrap NHS-activated column (Pharmacia Biotech) in a similar manner to that described in Example 2. The column was used to obtain eluates from soluble whole louse antigen prepared as described in Example 1.

Figure 7:
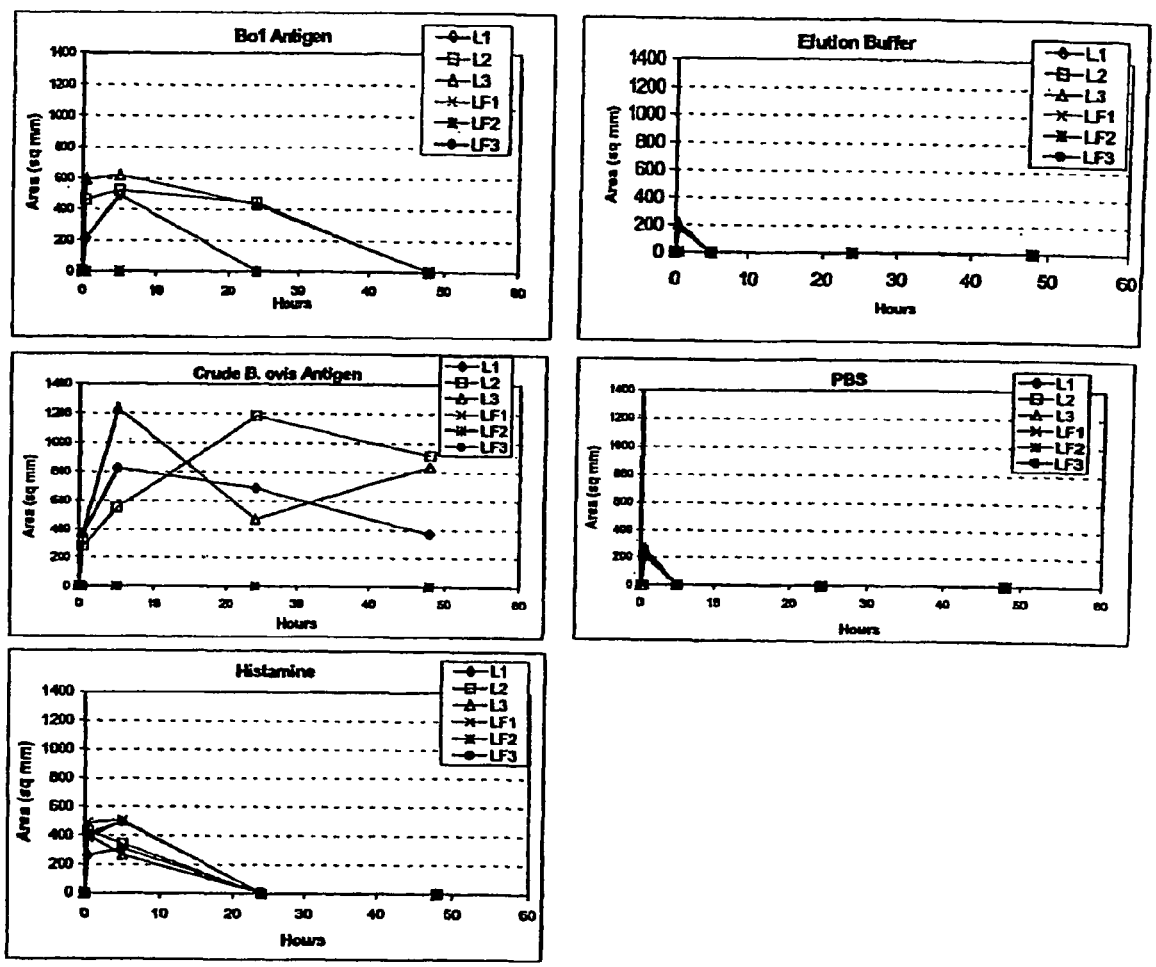
FIG. 7. shows the skin test results obtained following intradermal injections of antigens and control solutions in 3 louse-infested (L1, L2, L3) and 3 louse-naive (LF1, LF2, LF3) sheep.

The eluates from the monoclonal antibody affinity column contained a protein at high levels of purity and with characteristics consistent with the protein observed in crude louse antigen by SDS PAGE (FIG. 1) and Western blots probed with the monoclonal antibody (FIG. 2). Additionally, the purified allergen was recognised by IgE from louse-infested sheep on Western blots and in ELISA (FIG. 8). Intradermal skin testing confirmed specific responsiveness to Bo1 in louse-infested lambs compared to louse-naive lambs (FIG. 7).

EXAMPLE 6

Amino Acid Sequencing of the Bo1 Allergen

Native Bo1 purified using the monoclonal antibody affinity column was subjected to SDS PAGE under reducing conditions and electroblotted to PVDF membrane (Problott™, Applied Biosystems) using standard techniques for preparing proteins for sequencing. The PVDF membrane was stained with 0.1% Ponceau S and the 28.5 kDa band was identified and cut out. The membrane pieces were briefly washed with methyl alcohol containing 0.1% triethylamine followed by 2 washes with methyl alcohol alone. Automated microsequencing was carried out on a gas phase instrument (470AR/120A/920A/610A, Applied Biosystems). The N-terminal amino acid sequence obtained was (a) SPTELDLRLLVETARDISVILFKNLHAGYN
    (SEQ ID NO: 3)

The Bo1 28.5 kDa band was also cut from gels following SDS PAGE under reducing conditions for in-gel trypsin digests. The in-gel tryptic digestion followed the protocol of Rosenfeld, J., Capdevielle, J., Guillemot, J. C. and Ferrara, P. (1992) In-gel digestion of proteins for internal sequence analysis after one- or two-dimensional gel electrophoresis, *Analytical Biochemistry* 203:173-179. Peptides eluted from the gel were then separated on a Phenomenex Jupiter C18 column (300 angstrom, 5 micron, 2×250 mm) attached to a microbore HPLC (PE Biosystems, 140A delivery system and 1000S Diode array detector). Selected peptides were sequenced on a PE Biosytems Procise protein sequencer (model 492) using chemicals and methods supplied by the manufacturer. The following sequences were obtained

| (b) | DISVILFK    | (SEQ ID NO: 4) |
| (c) | NLHAGYNEVNPK | (SEQ ID NO: 5) |
| (d) | VFTNIK      | (SEQ ID NO: 6) |
| (e) | IGEQVLK     | (SEQ ID NO: 7) |
| (f) | (I)NVIFK    | (SEQ ID NO: 8) |

-continued (g) KLFDTEVPEVVK (SEQ ID NO: 9)
(h) DISVTLFK (SEQ ID NO: 10)
(i) IEILLNELAPEAK (SEQ ID NO: 11)
(j) TLIGALDQ(L)K (SEQ ID NO: 12)

EXAMPLE 7

RNA Isolation and cDNA Library Construction

RNA was isolated from B. ovis essentially as described by Frenkel M. J., Savin K. W., Bakker R. E., and Ward C. W. (1989). Characterization of cDNA clones coding for muscle tropomyosin of the nematode Trichostronglus colubriformis, *Molecular and Biochemical Parasitology*. 37:191-200. B. ovis (100 mg) snap frozen in liquid nitrogen were ground with a pestle and mortar over liquid nitrogen. One ml of 6 M Guanidine-HCL, 0.2 M sodium acetate (pH 5.2) plus 10 mM β-mercaptoethanol was added, ground with the B. ovis and the powder transferred to an eppendorf tube. Two hundred µl of 95% ethanol was added and the mixture placed on dry ice/ethanol for 5 minutes. The mixture was centrifuged for 5 minutes at 4° C. and the pellet then resuspended in 500 µl of 6 M Guanidine-HCL, 0.2 M sodium acetate (pH 5.2) plus 10 mM EDTA. Ethanol precipitation and centrifugation was repeated and the pellet resuspended in 250 µl of urea buffer (7M urea, 100 mM Tris-HCL (pH 7.5), 0.1 mM EDTA, 0.1% (w/v) SDS and then 500 µl of water saturated phenol:chloroform (1:1) was added. After centrifugation for 10 mins at 4° C. the aqueous layer was transferred to a new tube and the RNA was ethanol precipitated, dried and resuspended in 50 µl of double distilled water.

A cDNA library was synthesized from the B. ovis mRNA using a ZAP-cDNA® Synthesis Kit (Stratagene). The cDNA was ligated into the bacteriophage lambda Uni-ZAPTM XR vector arms with T4 DNA ligase and packaged with GIGA-PACK® II Packaging Extract.

EXAMPLE 8

Cloning and Characterisation of the Complete Coding DNA for Bo1

Based on the Bo1 amino acid sequences, an oligonucleotide primer (BoP14-A) was designed to hybridise to Bo1 cDNA encoding the amino terminal region (amino acid sequences (a), (b), (c) and (h) in Example 6) and a second oligonucleotide (BoP14-B) was designed to hybridise to Bo1 cDNA encoding an internal peptide (amino acid sequence (g) in Example 6). The oligonucleotides were designed to hybridise to opposing strands of the cDNA such that they would amplify the intervening cDNA when used as primers in a polymerase chain reaction (PCR) with cDNA derived from B. ovis mRNA.

| | |
|---|---|
| BoP14-A | CATGCTGGATATAATGAAGT(A/T)AA(C/T)CC (SEQ ID NO: 13) |
| BoP14-B | TTAACAACTTCAGGAACTTC(A/T)GT(A/G)TC(A/G)AA (SEQ ID NO: 14) |

The conditions for the PCR reaction were primers at 0.3 μM, dNTPs at 200 μM and 20 ng of template, 3 cycles of 94° C. for 30 sec, 45° C. for 60 sec and 72° C. for 60 sec; 30 cycles of 94° C. for 30 sec, 50° C. for 60 sec and 72° C. for 60 sec; and then held at 72° for 10 min.

Following PCR, an amplified DNA fragment of approximately 390 bp was identified by agarose gel electrophoresis. This fragment was purified using the Wizard® PCR Preps DNA Purification System (Promega) and then radiolabeled with [α-$^{32}$P]dCTP using the RTS RadPrime DNA Labelling System (Life Technologies). The radiolabeled Bo1 cDNA probe was used to screen the *B. ovis* cDNA library to identify DNA clones homologous to the Bo1 cDNA essentially as described in Sambrook, J., Fritsch, E. F. and Maniatis T. (1989). *Molecular cloning: a laboratory manual*, 2nd ed. New York (Cold Spring Harbour Laboratory Press). Approximately 45 000 phage clones from the library were plated onto agar plates with *E. coli* XL1-Blue MRF' cells and incubated to produce phage plaques. The plaques were replicated onto Hybond-N+ nylon membranes (Amersham) and processed for hybridisation with the probe. Positive hybridising clones were identified and these were plaque purified until they were clonal. The *B. ovis* cDNA inserts were amplified by PCR using primers that hybridised to the DNA surrounding the cDNA cloning site and the PCR products were sequenced. From the sequences, the complete coding sequence of the Bo1 allergen could be discerned (SEQ. ID No. 1). The sequence predicts a protein of approximately 30 kDa having an amino terminal secretory leader sequence. From the nucleoli sequence, the amino acid sequence (SEQ. ID No. 2) was deduced using codon preferences recognised for *B. ovis* and the N-terminal and internal sequences determined in Example 6.

EXAMPLE 9

Expression of Recombinant Bo1 Protein

The coding cDNA for the mature Bo1 protein, as predicted from the N-terminal amino acid sequence (Example 6, amino acid sequence (a)), was amplified by PCR from a *B. ovis* cDNA template. The oligonucleotide primers used in the PCR reaction to amplify the Bo1 cDNA were designed from the cDNA sequence obtained above (SEQ. ID. No. 1). The primers were

| | |
|---|---|
| Bo1-X2 | CTTGCGGCCGCCATTTTTGCAACACAGTCTG (SEQ ID NO: 15) |
| Bo1-X3 | CGCGGATCCATATGTCCCCAACAGAACTCGAT (SEQ ID NO: 16) |

Primer Bo1-X2 was designed to be homologous to the Bo1 cDNA encoding the amino terminus of the mature protein as identified by amino acid sequencing of the intact, purified Bo1 protein (amino acid sequences (a) in Example 6). Primer Bo1-X3 was designed to be homologous to the carboxyl terminal Bo1 amino coding DNA (SEQ. ID. No. 1). The primers also contained restriction enzyme cleavage sites to permit the ligation of the amplified DNA into an expression vector. Following a standard PCR reaction (35 cycles of 95° C. for 30 sec, 50° C. for 30 sec, and 72° C. for 1 min) with Bo1-X2 and Bo1-X3 primers and the Bo1 cDNA template, the product of approximately 700 bp was resolved by agarose gel electrophoresis. This PCR fragment was digested by NdeI and NotI endonucleases and cloned into the AY2-4 vector, a derivative of pBAD18 (Guzman, L., Belin, D., Carson, M. J. and Beckwith, J. (1995). Tight regulation, modulation, and high-level expression by vectors containing the arabinose PBAD promoter. *J. Bacteriol.* 177:4121-4130. ), resulting in the Bo1 expression vector shown in FIG. 3. Joining of the amplified coding DNA to the expression vector resulted in the fusion of the complete mature Bo1 coding sequence to the initiator methionine codon of the expression vector at a Nde1 restriction enzyme cleavage site. The carboxyl coding end of the Bo1 cDNA was joined at a Not1 site to vector DNA in frame with DNA encoding the E-tag epitope (Pharmacia) and the nonapeptide AAAHHHHH followed by a termination codon. The expression vector drives expression of the ligated coding DNA from the arabinose PBAD promoter and thus when electroporated into *E. coli* XL2, recombinant Bo1 is produced in response to exogenous arabinose in the growth medium (Guzman, L., Belin, D., Carson, M. J. and Beckwith, J. (1995). The recombinant Bo1 produced in this way has a carboxyl terminal fusion that includes the E-tag epitope and the nonpeptide AAAHHHHHH.

The transformed *E. coli* were induced to express the recombinant Bo1 by the addition of 0.2% L(+)arabinose to the culture medium (Luria-Bertani medium, Sigma, with Ampicillin, Sigma, at 100 µg/ml). The expressed recombinant protein was produced in the bacterial cytosol and was extracted by sonication of the bacteria and centrifugation to remove insoluble material. The recombinant Bo1 (rBo1) was then purified by immobilised metal affinity chromatography exploiting the affinity of the hexahistidine tag at the carboxyl terminus for immobilised nickel (HiTrapTM Chelating column, Amersham Pharmacia Biotech AB) and eluted with immadazol medium of increasing concentrations. Some preparations of rBo1 were further purified over the Bo1 mAb affinity column (Example 5). Because the recombinant protein has the carboxyl terminal fusion partner, it has a higher rMW (approximately 29.5 kDa) than the native protein on SDS PAGE under reducing conditions (FIG. 4).

The rBo1 was recognised by the Bo1 mAb on western blots (FIG. 4) and in ELISA. In preliminary trials, rBo1 was also recognised preferentially in ELISA by IgE from louse-infested sheep compared to louse-naive sheep.

EXAMPLE 10

The Specificity of Bo1 mAb for *B. ovis*

Figure 5:
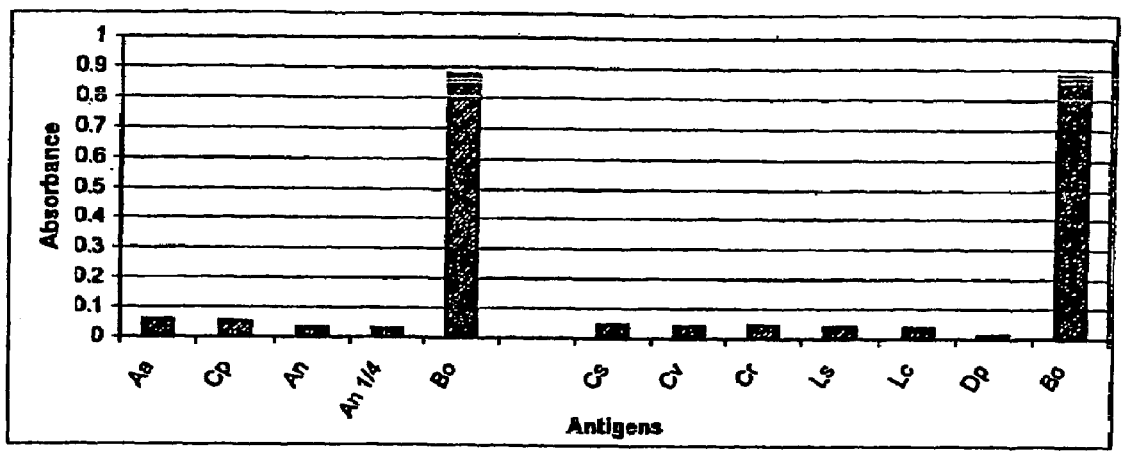
FIG. 5. shows the determination of the cross-reactivity of a Bo1 monoclonal antibody with soluble antigens of selected insects and a mite.

The specificity of Bo1 mAb for *B. ovis* was examined in ELISA by determining its reactivity with soluble antigen preparations made from a representative variety of insects to which sheep may be exposed in New Zealand and a mite. The antigens were prepared from adult sandflies, adult mosquitoes, and maggots of blowflies by crushing the insects in glass homogenisers in cold PBS containing 1 mM Pefabloc® (Boehringer Mannheim). Antigen preparations were clarified by centrifugation. *B. ovis* antigen was prepared as described in Example 1. *D. pteronyssinus* antigen was obtained commercially (Allergenic Extract, Standardized Mite DP, Bayer Corporation). After suitable dilution, the antigens were used to coat wells in microtitre plates and the ELISA performed using the Bo1 mAB as the primary antibody, and goat anti-mouse IgG conjugate as the second antibody using standard protocols. Bo1 mAb showed substantial reactivity only with antigen prepared from *B. ovis* (FIG. 5).

EXAMPLE 11

Use of *B. ovis*-specific Antibody in an in vitro Diagnostic Assay to Detect Louse Infestation An antigen capture ELISA was used to test for the presence of Bo1 on the wool of louse-infested and louse-naive lambs as shown in the following example.

Twenty-nine louse-infested and 12 louse-naive lambs, maintained at pasture, were scored for levels of louse infestation by counting the total number of lice observed in 10 cm long wool partings at 12 predetermined sites over the body. Wool samples were cut at skin level from the mid-shoulder region of these lambs and placed in individual paper bags and stored at room temperature. One gram of wool from each sample was placed in a glass container and mixed with 20 ml of buffer (PBS plus 0.5% Tween 20) for 2 hours at room temperature. The supernatants were decanted and used in the following antigen capture ELISA.

Monoclonal antibody specific for Bo1 (Bo1 mAb) was purified from hybridoma supernatants over a Protein G affinity chromatography column (Pharmacia) and concentrated using a 30 kDa Ultrafree® −15 Centrigual Filter Device (Millipore). Half of the purified Bo1 mAb was biotinylated with NHS-LC-biotin (Pierce) according to the manufacturer's recommendations. Maxisorp™ microtitre plates (Nunc) were coated with unbiotinylated Bo1 mAb in PBS (2 µg/ml) for 2 hours at room temperature, washed 3 times with wash buffer (150 mM NaCl, 0.05% Tween 20 in 10 mM phosphate buffer, pH 7.2), and blocked with blotto (10 mM phosphate buffer, containing 0.5% Tween 20, pH 7.2) and 5% bovine skim milk powder. Following a further 6 washes, undiluted extracts from the wool samples, positive controls (crude soluble antigen from whole lice in PBS) and negative controls (PBS plus 0.5% Tween 20) were then added to the plates in duplicate for 1 hour at room temperature. Plates were washed again 6 times and biotinylated Bo1 mAb (2 µg/ml) added for 1 hour at room temperature. Following 6 washes, strepavidin-horseradish peroxidase conjugate (2 µg/ml) was added for 1 hour. The enzyme reaction was developed using tetramethylbenzidine substrate, the reaction was stopped with 1 M sulphuric acid and adsorbance of the wells read at 450 nm wavelength.

Figure 6:
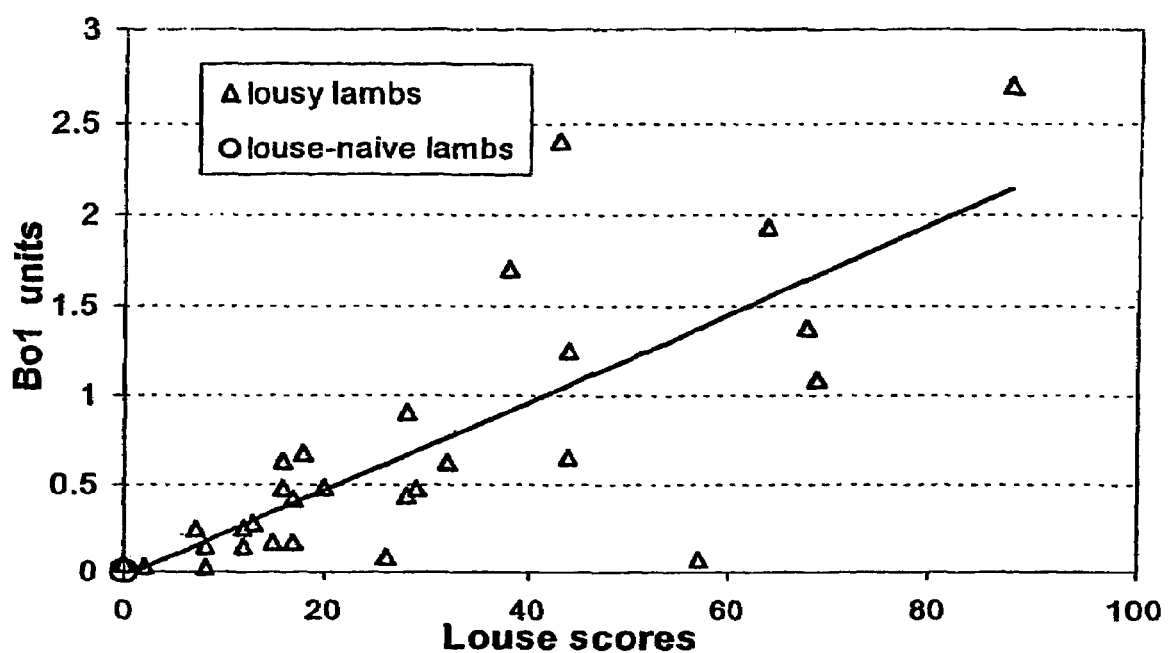
FIG. 6. shows the levels of Bo1 antigen detected in wool samples using an antigen capture ELISA employing Bo1 monoclonal antibody compared to louse scores in lambs.

All 12 louse-naive lambs had zero louse scores and were negative in the ELISA (FIG. 6). Results from the 29 louse-infested lambs were significantly correlated with the louse scores ($r=0.77$, $P<0.001$, FIG. 6). This assay can be used to detect louse infestation in sheep flocks and thereby assist farmers in the rational use of anti-louse treatments with consequent reduction of chemical residues in products from sheep and in the environment.

EXAMPLE 12

Diagnosis of Immunological Hypersensitivity to *B. ovis* in vivo by Intradermal Skin Testing Using Purified Bo1 Antigen Three louse-naive lambs and three louse-infested lambs, 12 months of age were used. The lambs were prepared for intradermal skin testing by closely shearing the wool from the upper shoulder region. The antigen and control solutions were injected intradermally in volumes of 0.1 ml. The diameters of the skin reactions were measured at 0.5, 5, 24, and 48 hours after injection. Bo1 was purified as described in Example 5. The Bo1 in neutralised elution buffer was diluted to approximately 6.0 µg per ml (determined by absorbance at 280 nm) with PBS. Neutralised elution buffer similarly diluted with PBS was the negative control solution for the Bo1. Crude soluble antigen prepared from whole *B. ovis* as described in Example 1 was diluted to 100 µg per ml. The negative control for crude *B. ovis* antigen was PBS mixed 1:1 with glycerol and similarly diluted. Histamine HCl (1 in 250000, w/v) in PBS was used to test for responsiveness to histamine.

The skin test results show substantial responses to crude *B. ovis* antigen and Bo1 only in the louse-infested sheep (FIG. 7). The responses within 30 minutes were typical of hypersensitivity due to reaginic (typically IgE) antibody-mediated mechanisms while responses extending to 5 hours and beyond indicate cellular mechanisms.

EXAMPLE 13

Use of Bo1 Antigen in an in vitro Assay to Detect Immunological Hypersensitivity to *B. ovis.*

An ELISA or similar assay may be used to detect IgE specific for Bo1 in sheep sera as an alternative to intradermal skin testing to diagnose hypersensitivity to *B. ovis*. Alternatively, similar assays can be used to detect other ovine immunoglobulin isotypes with specificity to Bo1 providing evidence of exposure of the host to the parasite.

To detect Bo1 specific IgE individual serum samples from sheep were treated with SAS (saturated ammonium sulphate solution) to reduce levels of competing IgG. 70% SAS in saline was added in a 1 to 1 ratio (v/v) to the serum samples for 30 minutes with periodic mixing. The precipitate was spun down (13 000 g, 10 minutes) and the supernatant diluted 1 to 8 in distilled water with 0.1% Tween 20 to give a final dilution of 1 in 16. Standard ELISA procedures were followed and are briefly described. Ninety-six well microtitre plates were coated with affinity purified Bo1 (1 in 100 in PBS) for 5 hours at room temperature. The plates were blocked with 10 mM phosphate buffer, pH 7.2, containing 0.5% Tween 20 and 5% bovine skim milk powder for 1 hour and then washed 6 times with wash buffer (150 mM NaCl, 0.05% Tween 20 in 10 mM phosphate buffer, pH 7.2). The SAS treated serums were added to duplicate wells and held at room temperature for 1 hour and then at 4° C. overnight. The plates were then washed 6 times with wash buffer and anti-ovine IgE monoclonal antibody in dilution buffer (5 mg/ml BSA, 0.1% Tween 20 in PBS) was added for 4 hours at room temperature. Following washing, goat anti-mouse IgG conjugated to horseradish peroxidase (Sigma A3673, 1 in 1000 in dilution buffer) was added for 1 hour at 37° C. The plates were washed again and tetramethylbenzidine (0.1 mg/ml, Sigma T8768) in 0.1M acetate buffer pH 6.5 plus 0.1% DMSO and 0.03% hydrogen peroxide added for 15 minutes. The reactions were stopped with 1 M sulphuric acid and absorbance at 450 nm read on an automated plate reader. The results from the ELISA using Bo1 were compared to a similar ELISA using crude *B. ovis* antigen (FIG. 8).

The ELISAs using whole louse antigen and purified allergen-coated plates showed significantly higher reactivity of serum IgE from lousy sheep than from louse-naive sheep ($P \leqq 0.0001$ and 0.0025 respectively, FIG. 8). Sixty-three percent (19/30) of the lousy sheep showed *B. ovis*-specific IgE absorbances greater than the mean plus 2 standard deviations of absorbances obtained using sera from louse-naive lambs (FIG. 8). The sera of 50% (15/30) of the louse-infested sheep showed elevated IgE absorbance to purified Bo1 allergen based on the same criteria. This data indicates that the purified allergen is a major allergen of *B. ovis*. In 13 of these sera, elevated IgE responses to both antigen preparations, were detected (FIG. 8). However, within the lousy sheep, only moderate correlation between the IgE responses to both antigen preparations was observed (r=0.49, P>0.006), suggesting the presence of other allergens in crude louse antigen and/or less non-specific reactivity when the purified Bo1 allergen is used.

DISCUSSION

The applicants have demonstrated serum antibody responses (including IgG and IgE) specific for antigens of the louse *B. ovis* and specific proliferation of lymphocytes obtained from skin draining lymph nodes in response to challenge with louse *B. ovis* antigens in vitro for the first time. Additionally, immunological responses to the louse have been demonstrated by intradermal skin testing where responses within one hour largely reflect the presence of reaginic antibodies (IgE and other homocytotropic antibodies) and persistence of responses to 24 hours and beyond largely reflect cell mediated mechanisms. The specificity of these various immunological responses was determined by comparing the responses in louse-infested lambs to those in louse-naive lambs maintained under similar conditions. The nature of the immunological responses to the louse and the character of the cockle lesions as determined by histology supports the concept that Cockle, the superficial dermatitis leading to pelt defects in louse-infested sheep, is the consequence of an allergic (or hypersensitive) immunological response to the louse. The novel allergen of the present invention and ligands binding to it may be used in diagnosis, prevention and treatment of *B. ovis* infection and the associated allergic disease resulting in improved wool and pelt quality, decreased use of synthetic insecticides and improved economic gains for the farmer.

It should be appreciated that throughout this specification wherever the term “comprises” (or grammatical variants thereof) is used, this term is not intended to be limiting and it does not exclude the presence of other features or elements in the present invention. Thus, the word “comprises” is equivalent to the word “includes”.

Aspects of the present invention have been described by way of example only, and it should be appreciated that modifications and additions may be made thereto without departing from the scope thereof as defined in the appended claims.

REFERENCES

Bany J, Pfeffer A and Phegan M (1995). Comparison of local and systemic responsiveness of lymphocytes in vitro to *Bovicola ovis* antigen and *Concanavalin* A in *B. ovis*-infested and naive lambs. International Journal for Parasitology 25:1499-1504.

Bany J, Pfeffer A, Phegan M and Heath A C G (1995). Proliferative responses of lymphocytes in *Bovicola ovis*-infested lambs. International Journal for Parasitology. 25:765-768.

Cleland P C, Dobson K J and Meade R J (1989). Rate of spread of sheep lice (*Damalinia ovis*) and their effects on wool quality. Australian Veterinary Journal. 66: 298-299.

Heath A C G, Cole D J W, Bishop D M, Pfeffer A T, Cooper S M, and Risdon P (1995). Preliminary investigations into the aetiology and treatment of Cockle, a sheep pelt defect. Veterinary Parasitology. 56:239-254.

Heath A C G, Cooper S M, Cole D J W and Bishop D M (1995). Evidence for the role of the sheep biting-louse Bovicola ovis in producing cockle, a sheep pelt defect. Veterinary Parasitology. 59:53-58.

Johnson P W, Boray J C, Plant J W and Blunt S C (1993). Prevalence of the causes of fleece derangement among sheep flocks in New South Wales. Australian Veterinary Journal 70:220-224.

Kettle P R and Lukies J M (1982). Effects of sheep lice (*Damalinia ovis*) on wool colour. New Zealand Journal of Experimental Agriculture. 10:15-17.

Kettle P R and Lukies J M (1984). Recovery of sheep lice (*Damalinia ovis*) from baled wool: a technique enabling nation-wide surveillance of louse ridden flocks. New Zealand Journal of Experimental Agriculture 12:39-42.

Lipson M and Bacon-Hall R E (1976). Some effects of various parasite populations in sheep on the processing performance of wool. Wool Technology and Sheep Breeding. pp18-20.

McLeod R S (1995). 'Costs of major parasites to the Australian livestock industries'. Proceedings of the Australian Society for Parasitology Annual Meeting, 1994. In the International Journal for Parasitology 25:1363-1367.

Pfeffer A T, Bany J, Phegan M D and Osborn P J (1993). 'Hypersensitivity skin testing of lambs infested with the biting louse (*Bovicola ovis*)'. Proceedings of the 23rd Conference of the NO Society for Veterinary and Comparative Pathology, November 1993. In New Zealand Veterinary Journal 42:76.

Pfeffer A, Phegan M D and Bany J (1997). Detection of homocytotropic antibody in lambs infested with the louse, *Bovicola ovis*, using a basophil histamine-release assay. Veterinary Immunology and Immunopathology 57:315-325.

Seymour-Jones A (1913) '"Cockle" in Sheepskins'. In The sheep and It's Skin, Seymour-Jones A. Leather Trades Review, London. Chapter VII, pp 204-221.

What is claimed is:

1. A method for diagnosing *Bovicola ovis* infestation in a host comprising
    obtaining an excretion, secretion, tissue or blood sample from the host; and
    exposing the sample to an antibody specific for an antigen Bo1 (SEQ ID NO: 2) present in the *Bovicola ovis* feces by an ELISA or radioimmunoassay, wherein said *Bovicola ovis* infestation is determined by the antibody having bound to said antigen.

2. The method of claim 1, wherein said Bo1 antigen is encoded by the nucleoli sequence of SEQ ID NO: 1.

* * * * *

UNITED STATES PATENT AND TRADEMARK OFFICE
CERTIFICATE OF CORRECTION

PATENT NO. : 7,294,477 B2
APPLICATION NO. : 10/258185
DATED : November 13, 2007
INVENTOR(S) : Pfeffer et al.

It is certified that error appears in the above-identified patent and that said Letters Patent is hereby corrected as shown below:

On the Title page, Col. 2 (Other Publications), please delete the 2nd to last reference "Pfeffer, A. et al.(1997) "Detection of homocytotropic antibody in lambs infested with the louse, *Bovicola ovis*, using a basophil histamine-release assay" *Veterinary Immunology and Immunopathology* 57:315-325."

On the Title page, line 1 of the Abstract, please delete "nucleoli" and insert --nucleotide--, therefore.

On the Title page, line 2 of the Abstract, after "and" please delete "a".

On the Title page, line 4 of the Abstract, please delete "nucleoli" and insert --nucleotide--, therefore.

In Col. 1, Line 14 (approx.), please delete "nucleoli" and insert --nucleotide--, therefore.

In Col. 1, Line 17 (approx.), please delete "nucleoli" and insert --nucleotide--, therefore.

In Col. 1, Line 64 (approx.), after "lambs" please insert --'--.

In Col. 3, Line 59 (approx.), please delete "nucleoli" and insert --nucleotide--, therefore.

In Col. 5, Line 36 (approx.), after "yet" please delete "a".

In Col. 6, Line 51 (approx.), please delete "nucleoli" and insert --nucleotide--, therefore.

In Col. 7, Line 14 (approx.), please delete "nucleoli" and insert --nucleotide--, therefore.

In Col. 7, Line 15 (approx.), please delete "nucleoli" and insert --nucleotide--, therefore.

In Col. 7, Line 17 (approx.), please delete "nucleoli" and insert --nucleotide--, therefore.

In Col. 7, Line 22 (approx.), please delete "nucleoli" and insert --nucleotide--, therefore.

In Col. 7, Line 30 (approx.), please delete "nucleoli" and insert --nucleotide--, therefore.

In Col. 8, Line 19 (approx.), please delete "nucleoli" and insert --nucleotide--, therefore.

In Col. 8, Line 49 (approx.), please delete "nucleoli" and insert --nucleotide--, therefore.

In Col. 8, Line 58 (approx.), please delete "nucleoli" and insert --nucleotide--, therefore.

In Col. 10, Lines 36 and 37 (approx.), please delete "*E. coli,*" and insert --*E. coli*--, therefore.

In Col. 10, Line 50 (approx.), after "(1983)" please insert --)--.

In Col. 17, Line 32 (approx.), after "SDS" please insert --)--.

CERTIFICATE OF CORRECTION (continued)
U.S. Pat. No. 7,294,477 B2

In Col. 18, Line 28 (approx.), please delete "nucleoli" and insert --nucleotide--, therefore.
In Col. 19, Line 19 (approx.), please delete "nonpeptide" and insert --nonapeptide--, therefore.
In Col. 32, Line 5 (approx.), Claim 2, please delete "nucleoli" and insert --nucleotide--, therefore.

Signed and Sealed this

Thirteenth Day of April, 2010

David J. Kappos
*Director of the United States Patent and Trademark Office*